US012755130B2

(12) United States Patent
Louisell, III et al.

(10) Patent No.: US 12,755,130 B2
(45) Date of Patent: Oct. 6, 2026

(54) SYSTEMS AND METHODS FOR IDENTIFYING TOXIC ELEMENTS IN WATER

(71) Applicant: True Elements, Inc., Naples, FL (US)

(72) Inventors: William C. Louisell, III, Mt. Pleasant, SC (US); David Bankston, Naples, FL (US)

(73) Assignee: True Elements, Inc., Naples, FL (US)

( * ) Notice: Subject to any disclaimer, the term of this patent is extended or adjusted under 35 U.S.C. 154(b) by 950 days.

(21) Appl. No.: 18/085,352

(22) Filed: Dec. 20, 2022

(65) Prior Publication Data

US 2023/0196060 A1 Jun. 22, 2023

Related U.S. Application Data

(60) Provisional application No. 63/292,051, filed on Dec. 21, 2021.

(51) Int. Cl.

| | |
|---|---|
| ***G06N 3/02*** | (2006.01) |
| ***G01N 33/18*** | (2006.01) |
| ***G06F 18/15*** | (2023.01) |
| ***G06F 18/2431*** | (2023.01) |

(52) U.S. Cl.

CPC ............... *G06N 3/02* (2013.01); *G01N 33/18* (2013.01); *G06F 18/15* (2023.01); *G06F 18/2431* (2023.01)

(58) Field of Classification Search

CPC . G06N 3/02; G06N 3/045; G06N 3/08; G06F 18/15; G06F 18/2431; G01N 33/18

See application file for complete search history.

(56) References Cited

U.S. PATENT DOCUMENTS

| | | | | |
|---|---|---|---|---|
| 5,646,863 | A * | 7/1997 | Morton | G01N 33/18 210/85 |
| 2021/0088448 | A1* | 3/2021 | Weng | G01N 33/2835 |
| 2023/0060380 | A1* | 3/2023 | Singh | G06F 16/215 |

* cited by examiner

*Primary Examiner* — Kathryn Elizabeth Limbaugh

(74) *Attorney, Agent, or Firm* — Michele V. Frank; Venable LLP

(57) ABSTRACT

Systems, methods, and computer-readable storage media for identifying toxic elements in water, and more specifically to identifying toxins in water based on sensor-detected contaminants and lists of known contaminants. A system can receive water contaminant data from sensors in a predefined geographic area, then normalize that water contaminant data. The system can also receive a list of categorized contaminants and use the list of categorized contaminants and a toxicity of the normalized water contaminants to score water toxicity for that predefined geographic area.

17 Claims, 6 Drawing Sheets

SYSTEMS AND METHODS FOR IDENTIFYING TOXIC ELEMENTS IN WATER

PRIORITY

The present application claims priority to U.S. provisional patent application No. 63/292,051, filed Dec. 21, 2021, the contents of which are incorporated herein in their entirety.

BACKGROUND

1. Technical Field

The present disclosure relates to identifying toxic elements in water, and more specifically to identifying toxins in water based on sensor-detected contaminants and lists of known contaminants.

2. Introduction

Water quality is of immense importance to not only human health, but also the well-being of environmental, animal, and agricultural concerns. To this end the EPA (Environmental Protection Agency) and others publish data, such as EPA Drinking Water Standards, EPA Discharge Monitoring Reports, the EPA Toxic Release Inventory, EPA Toxicity Factor Indexes, and various other EPA sources that identify the nature of health hazards associated with specific contaminants. While having a list of contaminants is useful for knowing what the EPA considers to be hazardous, it is not particularly helpful in identifying how clean, or toxic, one's water is.

For example, while knowing what contaminants are present in a water supply is important, often the combinations of those contaminants can result in water which is more toxic than when any single contaminant is present. Because of this, estimating the overall toxicity of the water in a given area can be difficult.

SUMMARY

Additional features and advantages of the disclosure will be set forth in the description that follows, and in part will be understood from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed are systems, methods, and non-transitory computer-readable storage media which provide a technical solution to the technical problem described. A method for performing the concepts disclosed herein can include: receiving, at a computer system from a plurality of sensors within a predefined geographic area, water contaminant data; normalizing, via at least one processor of the computer system the water contaminant data, resulting in normalized water contaminants; receiving, at the computer system from a database, a list of categorized contaminants; and scoring, via the at least one processor using the list of categorized contaminants, a toxicity of the normalized water contaminants, resulting in a water toxicity score for the predefined geographic area.

A system configured to perform the concepts disclosed herein can include: at least one processor; and a non-transitory computer-readable storage medium having instructions stored which, when executed by the at least one processor, cause the processor to perform operations comprising: receiving, from a plurality of sensors within a predefined geographic area, water contaminant data; normalizing, the water contaminant data, resulting in normalized water contaminants; receiving, from a database, a list of categorized contaminants; and scoring, using the list of categorized contaminants, a toxicity of the normalized water contaminants, resulting in a water toxicity score for the predefined geographic area.

A non-transitory computer-readable storage medium configured as disclosed herein can have instructions stored which, when executed by a computing device, cause the computing device to perform operations which include: receiving, from a plurality of sensors within a predefined geographic area, water contaminant data; normalizing, the water contaminant data, resulting in normalized water contaminants; receiving, from a database, a list of categorized contaminants; and scoring, using the list of categorized contaminants, a toxicity of the normalized water contaminants, resulting in a water toxicity score for the predefined geographic area.

DETAILED DESCRIPTION

Figure 1:
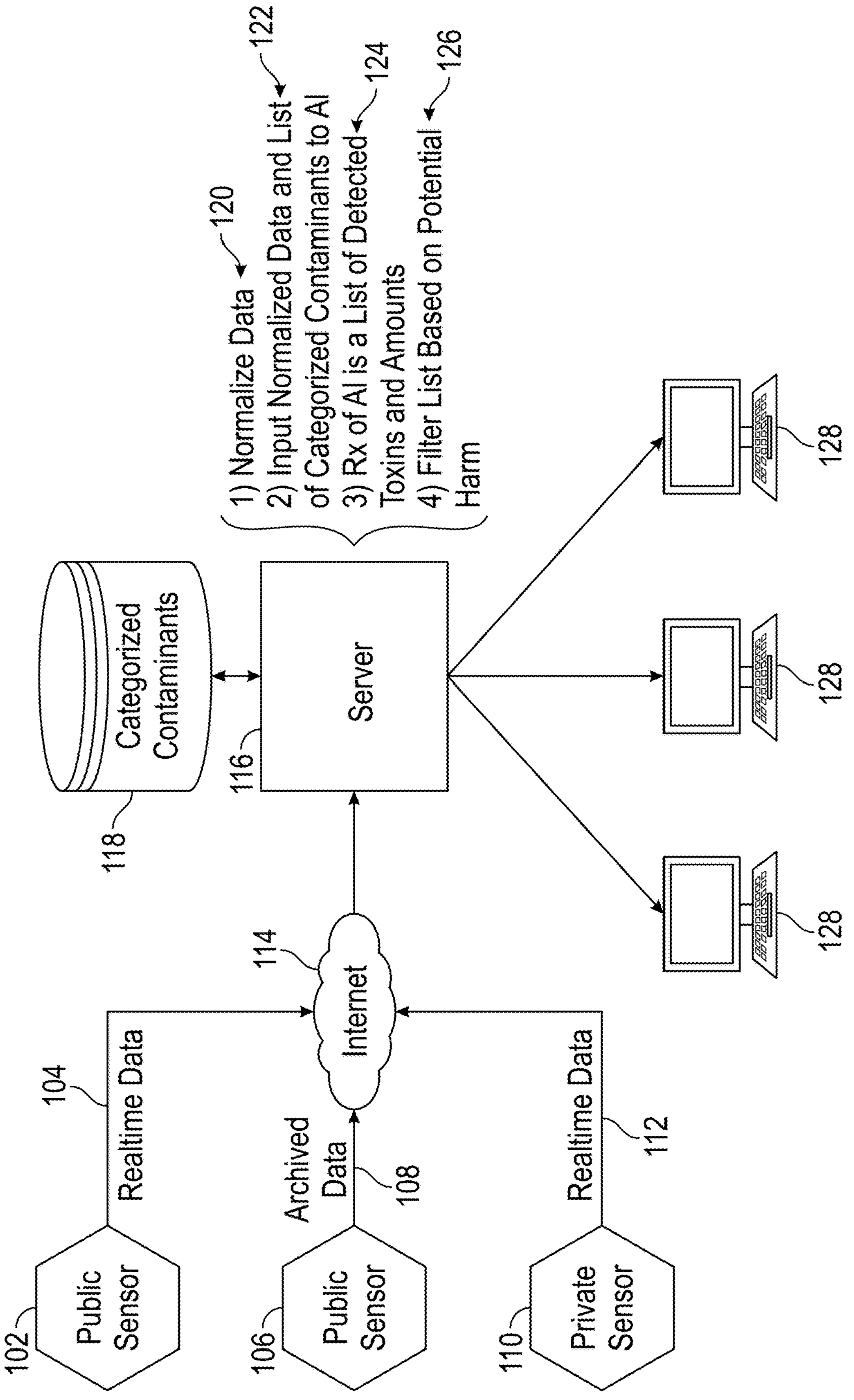
FIG. 1 illustrates an example system embodiment.

Various embodiments of the disclosure are described in detail below. While specific implementations are described, it should be understood that this is done for illustration purposes only. Other components and configurations may be used without parting from the spirit and scope of the disclosure.

In order to determine one's water quality, one needs to identify what is in their water of interest and then compare that with the various sources (such as EPA (Environmental Protection Agency) sources or other private sources) that provide information on various hazards, i.e. health hazards (reproductive/generational effects, cancer potential, long-term/chronic condition potential, and minor & temporary skin rash/discomfort & digestive effects), cosmetic hazards (tooth, eye, and/or skin discoloration), water color and odor issues, and effects on the technical aspects of water infrastructure (pipe deterioration, scale in tank systems, etc.). In addition, the EPA also publishes toxicity information on contaminants found in both water and air, as well as water borne contaminants that evaporate and/or atomize such that they become air borne.

Systems configured as disclosed herein allow for understanding the full range of constituency, understanding the singular effect and toxic level of each contaminant, and understanding the potential for amplification of effects when combined with other contaminants or materials. The result is a continuously updated, single-source listing of water quality contaminants of interest, the relative health or non-health effect of each contaminant, the various nomenclatures which relate to the root generator of health and/or non-health effects, and a reference system to understand holistically the quality of water.

A first problem is that there is no single complete list of contaminants that provides a perspective of precedence in terms of hazard because there is no normalized means of indexing items from the drinking water regulations and from the catalog of environmental toxins. A second problem exacerbates the issue by the fact that knowing what is in your water is a complicated process with many different reference data sources that do not share common vernacular. A contaminant listed in one source may be framed in one way, while in another source that same contaminant may be referenced in a different format or by a lay expression of the contaminant's identity. A third problem is that the population of agricultural, stormwater, industrial, water treatment, and wastewater treatment contaminants is constantly evolving. For example, a new brake lining material for cars may use a new form of an old material or a completely new compound that includes formerly singularly identifiable materials. These new forms of old and or newly combined contaminants should be considered in the evaluation of water quality.

The systems and methods described herein address these problems. First, a system configured as described herein can use a natural language interpretation system to assign classes of effects. Second, the system can use artificial intelligence (AI) to stratify contaminants within an indexing system, providing a normalized means of comparison. Third, the system can employ a custom web-scraping capability to examine the authoritative sites of organizations that track and report on the ever-evolving means and methods of manufacturing, and the continually changing descriptions, of materials that have become present in new forms. These materials can be traced in lineage to EPA catalogued forms for which class of effect and toxicity data can be derived. The system can also recognize that some aspects of water quality measurement are not in and of themselves hazardous but, at various levels (e.g., elevated pH), the effect and toxic impact on humans, animals, and plants can be different. To that end, the system can catalog these physical properties such that they can be used to predict cases in which a certain contaminant or in basket of contaminants may have effects not anticipated under normal circumstances. For example, in the case of a wildfire, large amounts of ash may find its way into a river, increasing pH. When this higher pH water arrives for induction into a municipal drinking water system, there can be unanticipated consequences, or there can be unintended consequences of application of mitigation measures to deal with the large amounts of ash.

Systems configured as described herein can rate water quality at any point in the water journey. For example, the system can rate the water quality of a drop of rain, water quality of surface water (overland & riverine), water quality of underground aquifers or wells, and the water quality within water pipes or other water delivery systems. To do this, the system uses a combination of sensors distributed throughout the body of water being analyzed, with these sensors capable of identifying specific chemicals or other contaminants within the water. The system also performs web scraping to capture current lists of water contaminants which are harmful to humans, animals, and plants such as (but not exclusive to) the EPA (Environmental Protection Agency) drinking water standards, EPA discharge monitoring Reports, EPA toxic release inventory, EPA toxicity factor indexes, and other EPA sources that identify the nature of health hazards associated with specific contaminants The system can take the list(s) of contaminants and perform stratification on the contaminants, thereby identifying different categories of how the contaminants effect health, environment, etc. The system can use an algorithmic classification and indexing method. Firstly, the method can identify the class and sub-class of a given contaminant. For example: class=health, sub-class=reproductive/generational effects, cancer potential, long-term/chronic condition potential, and/or minor & temporary skin rash/discomfort & digestive effects; class=cosmetic hazards, sub-class=tooth, eye, and/or skin discoloration; class=water color & odor issues, sub-class=color, odor; and class=technical effects, sub-class=pipe deterioration, scale, etc. The system can then sort the contaminants listed within the classes and sub-classes in terms of toxicity index (ingestion index, inhalation index and, for those not considered in the drinking water regulations, they can be separated into class based on if they are carcinogenic.

The data, representing measurements throughout the body of water being analyzed, can be tied back to which contaminants are expected, and in what quantities. The system can normalize this data, and using the normalized data and the categorized contaminants, identify contaminants and/or toxins (e.g., combinations of one or more contaminants) within the water which meet threshold standards for causation of health or non-health effects. Normalization can be accomplished via a computational routine. Stratification can be within the particular interest defined as class and/or sub-class (as described above), if applicable, with an index tier 1-5 with tier 1 having the most significant effect and tier 5 having the least. For a class or sub-class agnostic assessment, the tier 1-5 determination is provided based on analysis of the toxicity index of interest (ingestion or inhalation) for all assessment included contaminants. Once the contaminant and/or basket of contaminants of interest has been defined by the user, a specific analytic routine unique to this invention can be used to bin each contaminant into a tier. Further computation to determine the impact of the contaminant(s) in terms of a 0-100 indexing system is accomplished. The final product of the process is an integer between 0 and 100 inclusive indicating the water quality. If, for example, the system detected chemical "A" with a density (e.g., $g/m^3$, g/L) "X," and chemical A is listed as a contaminant within the categorized contaminants, the system can first verify that chemical A is listed, and then determine if the density of chemical A (X) exceeds a threshold. If so, the system can report chemical A as meeting an index value associated with a predetermined level of concern (e.g., "85"). Likewise, if the combination of chemicals A and "B" resulted in a lower index value (e.g., "68"), the system can review and report the combined effect of A and B separately from that of A alone.

In some configurations, the contaminants and/or toxins can have different levels of danger depending on the measured density. Returning to the example of chemical "A," the system may report a first level of danger if the system detects a first amount or density of A, a second level of danger if the system detects a second amount or density of A, and so on.

Based on the potential harm determined from EPA or other sources, associated with the various contaminants/toxins, the system can filter out which contaminants are reported to end user who seeks to know the water quality. For example, if a contaminant is detected so far below the danger threshold that it has no harm, the system can filter reporting of that contaminant. Other contaminants, which can potentially cause harm or danger, can be reported to the end user along with an overall score indicating the water quality for that body of water.

In some configurations, the system can use Artificial Intelligence (AI) to combine identify one or more toxins from the detected contaminants. For example, the system can train a neural network to recognize combination toxins from a list of individual contaminant or chemicals detected by sensors. To this end, the system can engage a structured stack of algorithms. At a base tier, the system makes a determination of the existing state with regard to the forecast state generated by the surface runoff models linked to underlying hydrologic and hydrographic models given conditions such as expected weather conditions (precipitation), season of the year, and/or land use (e.g., urban, agriculture, industrial, pasture/grasslands, forest, scrub and/or barren). A second tier searches sensed measurements (e.g., physical, biological and/or directly sensed contaminant properties). A third tier searches industrial and other discharge permits (e.g., federal, state, and/or local permits) to determine the probable constituency. A fourth tier searches for time and location of relevant public and/or environmental notifications (e.g., via social media scraping techniques) for spills or leaks. Managing this multi-tier AI structure is a controller that can assign weighted probability of the presence of chemicals individually and/or in combination, and can produce base metric values indicating that presence based on the data collected in the underlying tiers (e.g., the first, second, and/or third tiers) The inputs to the neural network could be, for example, the sensor data, such as detection of individual chemicals or contaminants. The neural network could then output detected toxins or combinations of those detected chemicals/contaminants. Training of the AI/neural network can occur via any method known to those of skill in the art, and can be combined with the continuous search and assessment of current and past public environmental impact events. Such assessments can be made from both a chemistry and/or and present condition point of view. This record, representing both quantitative and qualitative data, can be driven by a human-guided digital corpus and a natural language corpus. As outputs are received from the AI/neural network system, experts can review the data and provide feedback regarding its accuracy. That feedback can be added to a corpus of training data, such that future iterations of the neural network are improved. This feedback process and iterative retraining of the neural network is referred to as "supervised learning."

The corpus of data can include data scrapped from sources such as EPA websites, medical journals, industrial chemical guidelines, etc., using underlying quantitative and qualitative data, is driven by a human-guided digital corpus and/or natural language corpus. The corpus can also contain a thesaurus or index linking multiple distinct names for a single chemical or contaminant, such that if a given industry uses a distinct name for a contaminant that that which is used by the EPA, the system can associate both names for the same chemical/contaminant.

In addition, the corpus of training data used to build the AI can increase over time using additional data acquired through web-scraping. As the system continues web-scraping, new data, or updated data, is added to the corpus. Periodically, or when the system reaches a threshold increase in data, the system can retrain the neural network using the updated training corpus. In some configurations, the neural network can prune or remove old data or intermediate nodes which are no longer useful in providing accurate outputs. Because constantly adding to the training corpus can result in ever-increasing training times for the AI, the ability to remove or prune data which is not useful to accurate outputs can result in saved computational time and/or power. For example, if industrial regulations change such that a different type of copper will be used in the future, the system can modify what type of copper is used in evaluating the toxicity of the water.

FIG. 1 illustrates an example system embodiment. As illustrated, multiple sensors 102, 106, 110 data regarding chemicals, contaminants, and/or other information regarding a body of water, and communicate that sensor data across the internet 114 to a server 116. In practice, the illustrated server 116 may be more than one server, or may be a cloud-based computing platform (such as AZURE or AMAZON WEB SERVICES). The server 116 receives the sensor data 104, 108, 112 (which can include realtime and archived data), and also receives a list of categorized contaminants from a database 118. The server 116, using at least one processor, normalizes 120 the sensor data, then inputs 122 the normalized data and/or the list of categorized contaminants into an AI algorithm, which can identify 124 contaminants and/or toxins within the water and their associated quantities and/or densities. The system 116 can then filter out 126 which of those contaminants and/or toxins are above a predefined threshold for potential harm, and give the body of water being analyzed a water quality score. The water quality score and/or the filtered contaminants/toxins can then be passed on to end users, or more accurately, transmitted electronically to the computer terminals 128 of the end users.

Figure 2:
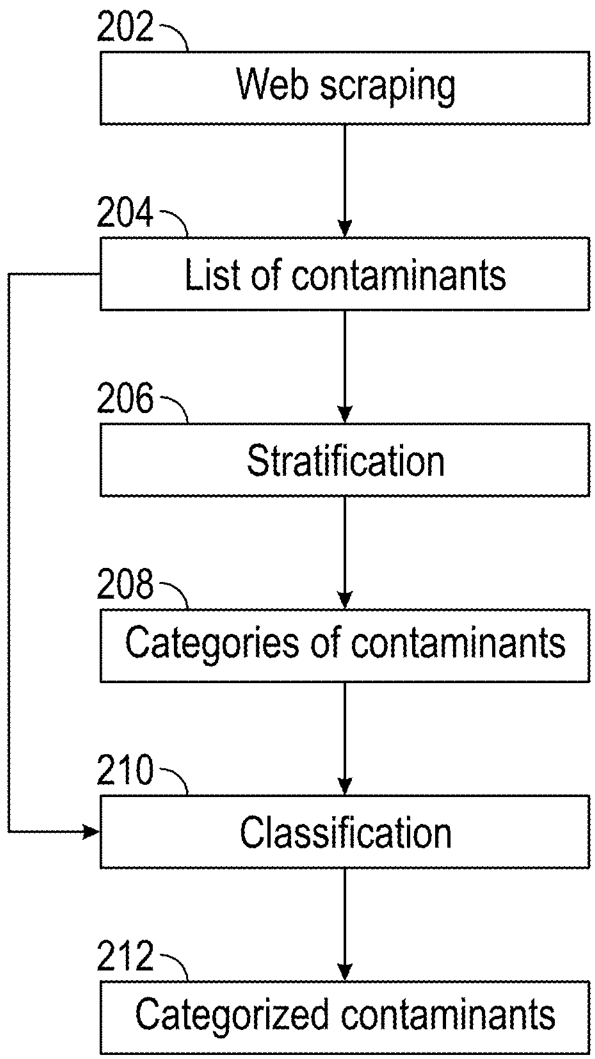
FIG. 2 illustrates an example process for categorizing contaminants.

FIG. 2 illustrates an example process for categorizing contaminants. In this example, the system performs web scraping 202 on websites such as those operated by the EPA (Environmental Protection Agency) which list contaminants, toxins, etc. Examples include the drinking water standards, EPA discharge monitoring Reports, EPA toxic release inventory, EPA toxicity factor indexes, and other EPA sources that identify the nature of health hazards associated with specific contaminants. The system scrapes 202 these websites, resulting in a list of contaminants 204, then performs stratification 206 of the contaminants within that list, resulting in categories or "buckets" 208 into which the different contaminants can be sorted. The system can then classify the contaminants into those categories, resulting in categorized contaminants 212.

Figure 3:
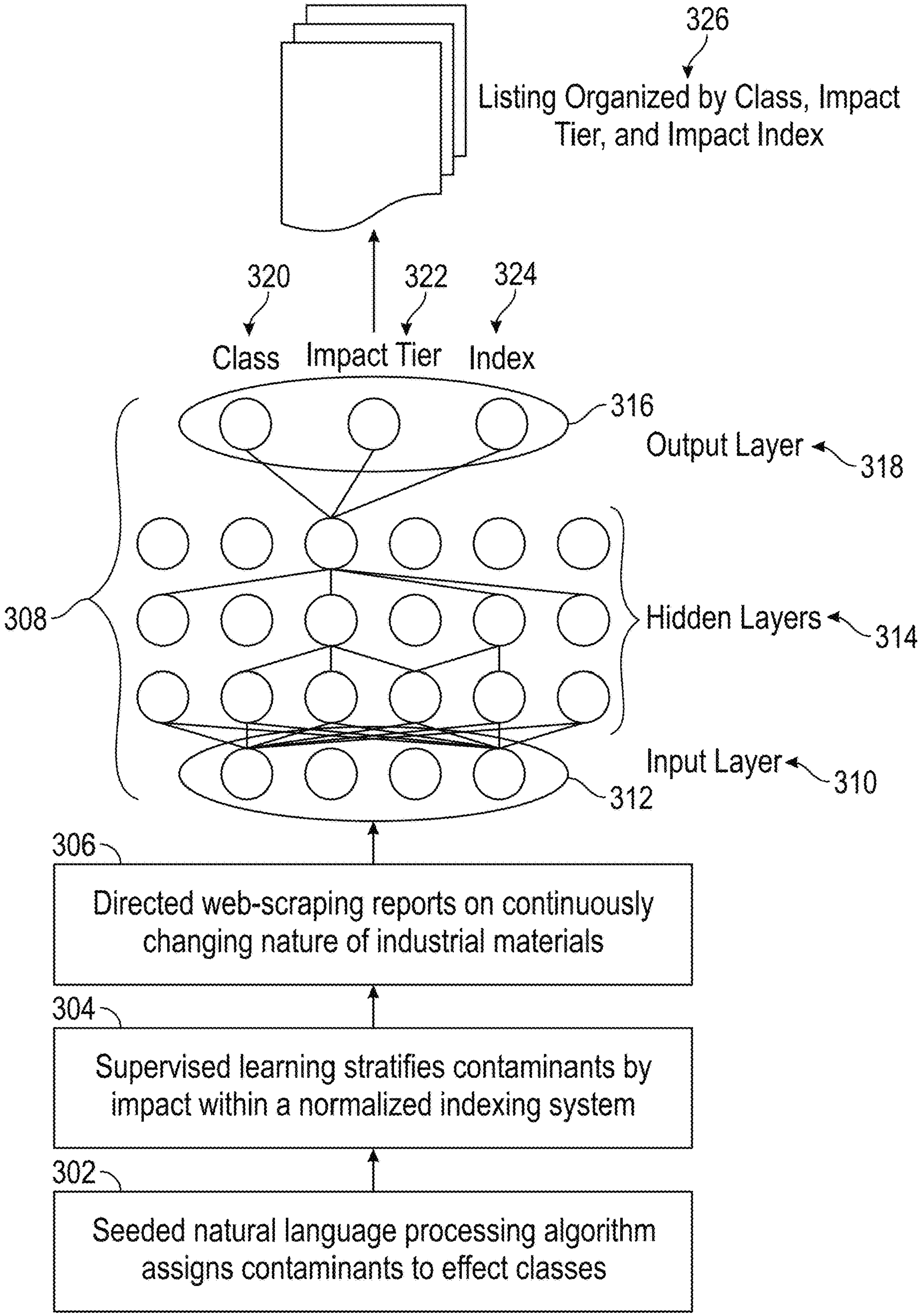
FIG. 3 illustrates an example of using web-scraped contaminant data to form a neural network.

FIG. 3 illustrates an example of using web-scraped contaminant data to form a neural network. As illustrated, the system can use seeded natural language processing to assign contaminants to effect classes 302, such as health, water color, technical effects, etc. The system can also use supervised learning to stratify contaminants by impact within a normalized indexing system 304. This supervised learning can, for example, present the outputs of the neural network to one or more experts in the field, who can review the results and provide feedback as to their accuracy. Based on that feedback from those experts, the system can "learn" to provide different or distinct outputs in the future. The system can also perform directed web-scraping to capture the latest information on the continuously changing nature of materials 306, such as industrial materials, pollutants, etc.

With this corpus of data, the system can generate a neural network 308 having an input layer 310 corresponding to specific inputs 312 of sensor data (which can, for example, indicate levels of detected contaminants); hidden layers 314 (which the system uses to identify relationships between different aspects of the data); and an output layer 318, which, in this case, include outputs 316 of the class(es) of the contaminants 320, the impact tier of the contaminants 322, and/or the impact index of the contaminants 324. This information can be organized and listed 326, then provided to a user wanting information associated with a particular body of water.

Figure 4:
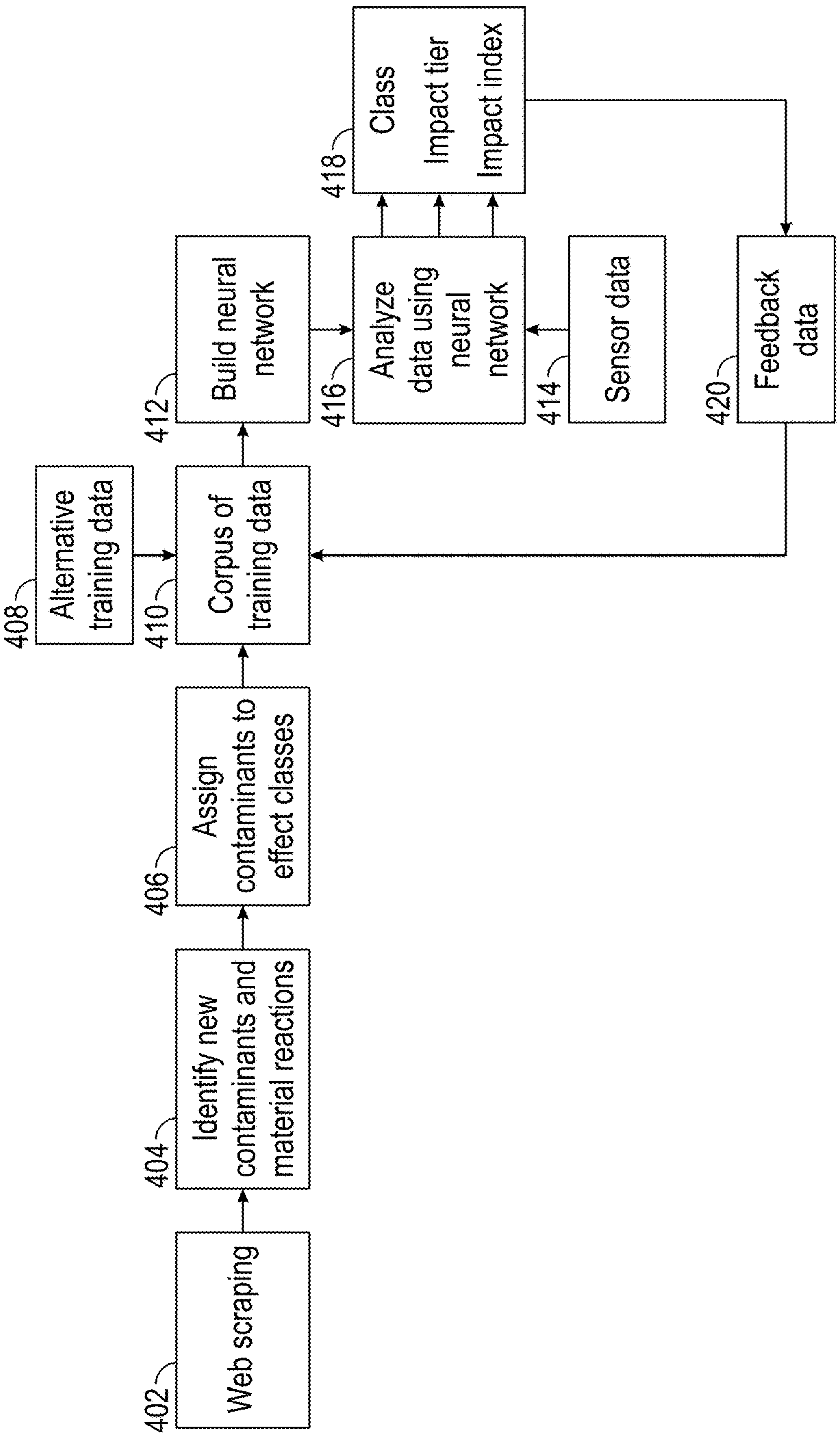
FIG. 4 illustrates an example of using feedback and additional training data to iteratively train the neural network.

FIG. 4 illustrates an example of using feedback and additional training data to iteratively train the neural network. Like the example of FIG. 3, this example illustrates web-scraping 402, followed by identifying new contaminants and material reactions 404 from that web-scraping. This can be done using, for example, Natural Language Processing (NLP) to identify relationships between the scrapped text. The system can then assign the contaminants to effect classes 406, such as health, water color, etc., as described above.

The result is a corpus of training data 410 which can be used to train/build a neural network 412, which, as described above, can be used to analyze/evaluate 416 sensor data 414, and output 418 class, impact tier, and an input index. However, in this case, the corpus of training data 410 also receives alternative training data 408. For example, the corpus 410 may receive data about how various chemicals interact with one another, and that information can be added to the corpus 410 such that future iterations of the neural network identify toxins or other multi-contaminant compounds in an improved manner. The corpus 410 can also receive feedback data 420, enabling the "supervised learning" discussed above. Furthermore, the web scraping 402 is not done in a single iteration. The web-scraping 402 can be done periodically or continuously, again adding to the corpus of training data 410. The retraining of the neural network 412 can occur periodically, such as every week or every month, and the updated neural network can replace the previous neural network. In practice, the system may overwrite the previous neural network in memory, however often the system may assign the updated neural network to a different memory location and assign execution of the updated neural network, rather than deleting the previous one initially.

Figure 5:
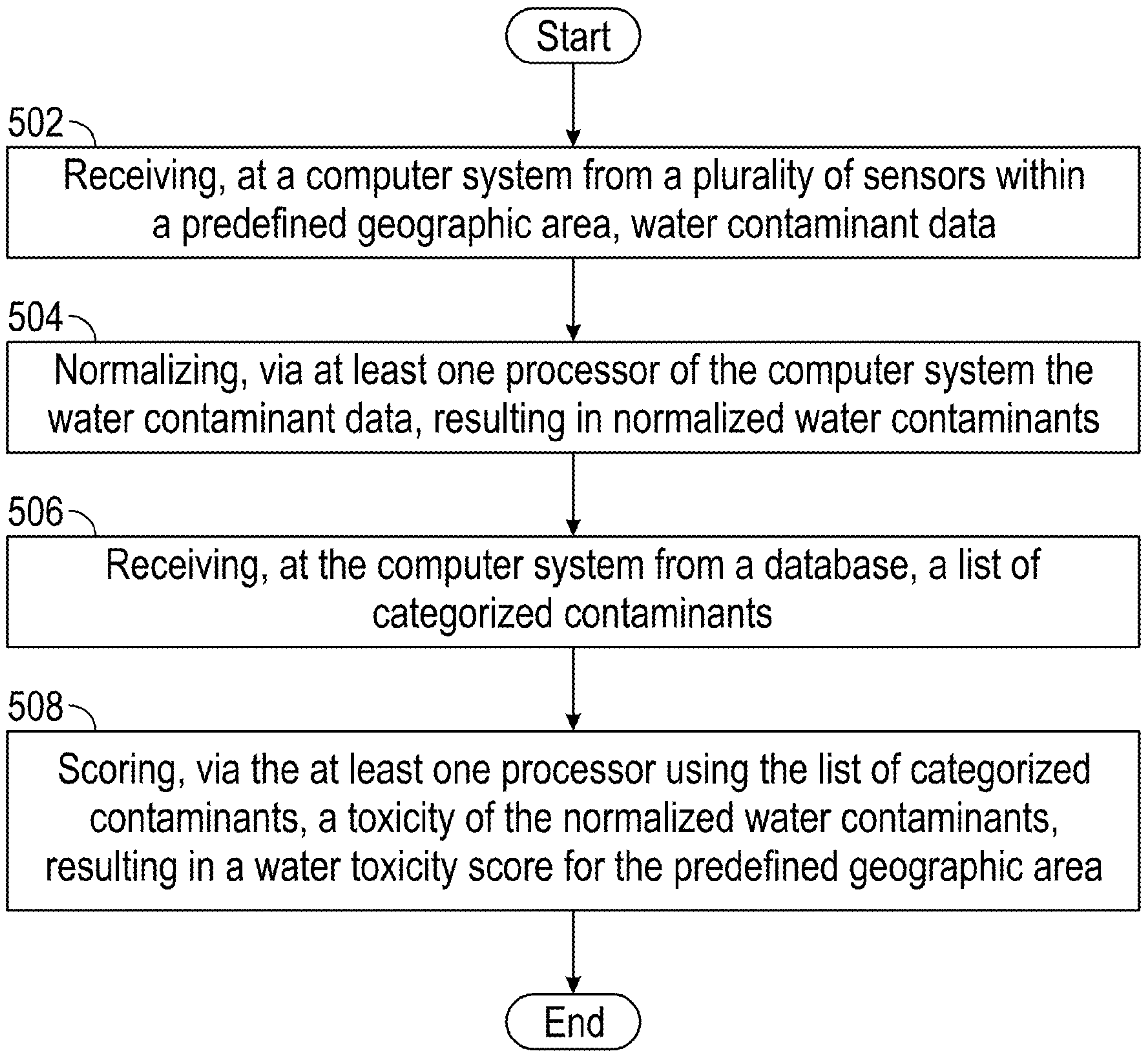
FIG. 5 illustrates an example method embodiment.

FIG. 5 illustrates an example method embodiment. As illustrated, the method can include receiving, at a computer system from a plurality of sensors within a predefined geographic area, water contaminant data (502), and normalizing, via at least one processor of the computer system the water contaminant data, resulting in normalized water contaminants (504). The method can then include receiving, at the computer system from a database, a list of categorized contaminants (506) and scoring, via the at least one processor using the list of categorized contaminants, a toxicity of the normalized water contaminants, resulting in a water toxicity score for the predefined geographic area (508).

In some configurations, the list of categorized contaminants can be generated by: receiving, at the computer system via web scraping, a list of water contaminants; stratifying, via the at least one processor, the list of water contaminants into categories based on commonalities, resulting in categories of contaminants; and classifying, via the at least one processor, the list of water contaminants into the categories of contaminants, resulting in the list of categorized contaminants. In such configurations, the list of water contaminants can be provided with a CAS (Chemical Abstracts Service) registration number of each chemical within the list of water contaminants.

In some configurations, the scoring of the toxicity of the normalized water contaminants can include executing, via the at least one processor, a artificial intelligence algorithm. In such configurations, the artificial intelligence algorithm comprises a neural network.

In some configurations, the water contaminant data can include both regulated and unregulated contaminants.

In some configurations, the illustrated method can include transmitting, from the computer system to a terminal computer in response to a request from the terminal computer, the water toxicity score.

Figure 6:
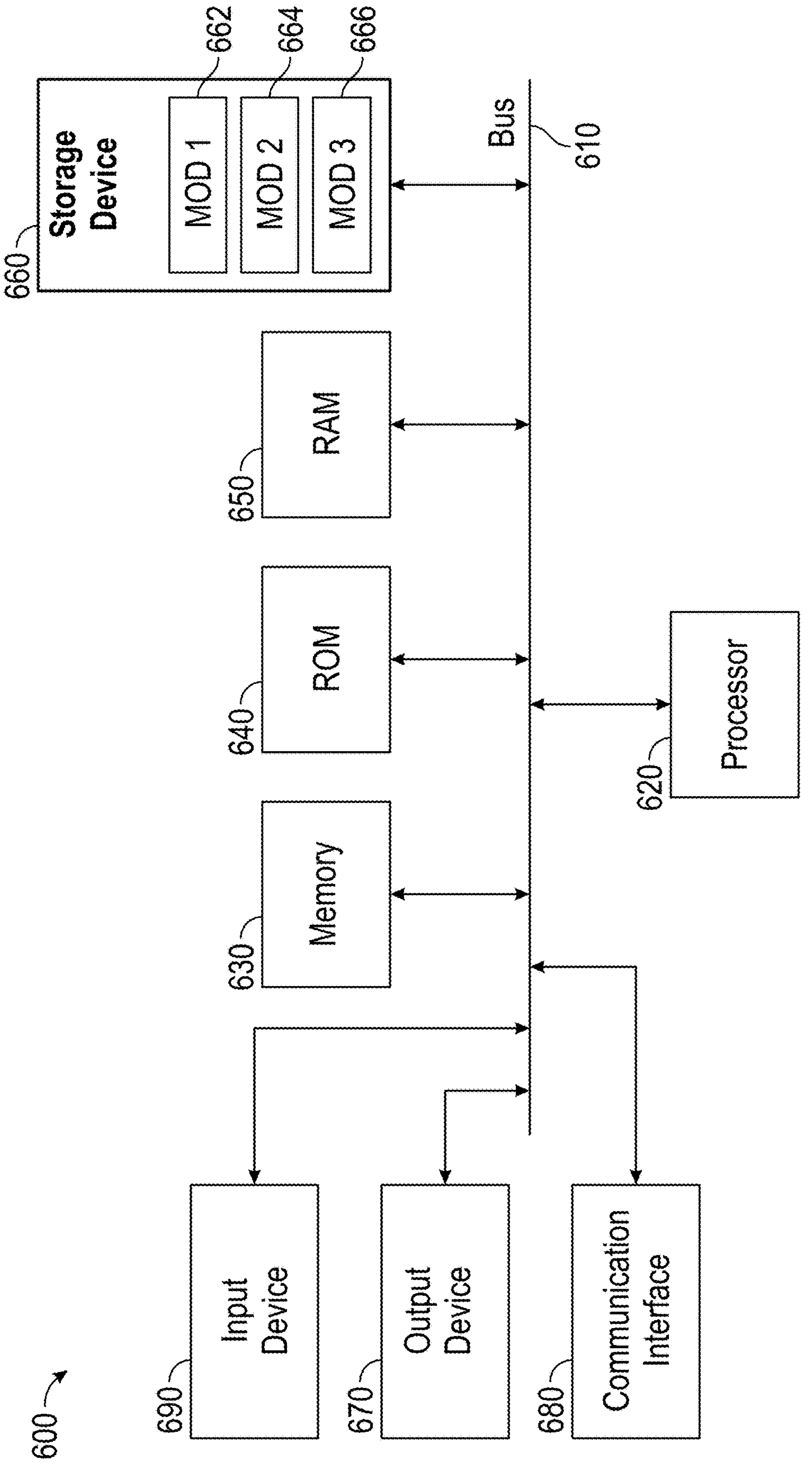
FIG. 6 illustrates an example computer system.

With reference to FIG. 6, an exemplary system includes a general-purpose computing device 600, including a processing unit (CPU or processor) 620 and a system bus 610 that couples various system components including the system memory 630 such as read-only memory (ROM) 640 and random access memory (RAM) 650 to the processor 620. The system 600 can include a cache of high-speed memory connected directly with, in close proximity to, or integrated as part of the processor 620. The system 600 copies data from the memory 630 and/or the storage device 660 to the cache for quick access by the processor 620. In this way, the cache provides a performance boost that avoids processor 620 delays while waiting for data. These and other modules can control or be configured to control the processor 620 to perform various actions. Other system memory 630 may be available for use as well. The memory 630 can include multiple different types of memory with different performance characteristics. It can be appreciated that the disclosure may operate on a computing device 600 with more than one processor 620 or on a group or cluster of computing devices networked together to provide greater processing capability. The processor 620 can include any general purpose processor and a hardware module or software module, such as module 1 662, module 2 664, and module 3 666 stored in storage device 660, configured to control the processor 620 as well as a special-purpose processor where software instructions are incorporated into the actual processor design. The processor 620 may essentially be a completely self-contained computing system, containing multiple cores or processors, a bus, memory controller, cache, etc. A multi-core processor may be symmetric or asymmetric.

The system bus 610 may be any of several types of bus structures including a memory bus or memory controller, a peripheral bus, and a local bus using any of a variety of bus architectures. A basic input/output (BIOS) stored in ROM 640 or the like, may provide the basic routine that helps to transfer information between elements within the computing device 600, such as during start-up. The computing device 600 further includes storage devices 660 such as a hard disk drive, a magnetic disk drive, an optical disk drive, tape drive or the like. The storage device 660 can include software modules 662, 664, 666 for controlling the processor 620. Other hardware or software modules are contemplated. The storage device 660 is connected to the system bus 610 by a drive interface. The drives and the associated computer-readable storage media provide nonvolatile storage of computer-readable instructions, data structures, program modules and other data for the computing device 600. In one aspect, a hardware module that performs a particular function includes the software component stored in a tangible computer-readable storage medium in connection with the necessary hardware components, such as the processor 620, bus 610, display 670, and so forth, to carry out the function. In another aspect, the system can use a processor and computer-readable storage medium to store instructions which, when executed by the processor, cause the processor to perform a method or other specific actions. The basic components and appropriate variations are contemplated depending on the type of device, such as whether the device 600 is a small, handheld computing device, a desktop computer, or a computer server.

Although the exemplary embodiment described herein employs the hard disk 660, other types of computer-readable media which can store data that are accessible by a computer, such as magnetic cassettes, flash memory cards, digital versatile disks, cartridges, random access memories (RAMs) 650, and read-only memory (ROM) 640, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 600, an input device 690 represents any number of input mechanisms, such as a microphone for speech, a touch-sensitive screen for gesture or graphical input, keyboard, mouse, motion input, speech and so forth. An output device 670 can also be one or more of a number of output mechanisms known to those of skill in the art. In some instances, multimodal systems enable a user to provide multiple types of input to communicate with the computing device 600. The communications interface 680 generally governs and manages the user input and system output. There is no restriction on operating on any particular hardware arrangement and therefore the basic features here may easily be substituted for improved hardware or firmware arrangements as they are developed.

Use of language such as "at least one of X, Y, and Z," "at least one of X, Y, or Z," "at least one or more of X, Y, and Z," "at least one or more of X, Y, or Z," "at least one or more of X, Y, and/or Z," or "at least one of X, Y, and/or Z," are intended to be inclusive of both a single item (e.g., just X, or just Y, or just Z) and multiple items (e.g., {X and Y}, {X and Z}, {Y and Z}, or {X, Y, and Z}). The phrase "at least one of" and similar phrases are not intended to convey a requirement that each possible item must be present, although each possible item may be present.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure.

Further aspects of the present disclosure are provided by the subject matter of the following clauses.

CLAIMS LISTING

A method comprising: receiving, at a computer system from a plurality of sensors within a predefined geographic area, water contaminant data; normalizing, via at least one processor of the computer system the water contaminant data, resulting in normalized water contaminants; receiving, at the computer system from a database, a list of categorized contaminants; and scoring, via the at least one processor using the list of categorized contaminants, a toxicity of the normalized water contaminants, resulting in a water toxicity score for the predefined geographic area.

The method of any preceding clause, wherein the list of categorized contaminants is generated by: receiving, at the computer system via web scraping, a list of water contaminants; stratifying, via the at least one processor, the list of water contaminants into categories based on commonalities, resulting in categories of contaminants; and classifying, via the at least one processor, the list of water contaminants into the categories of contaminants, resulting in the list of categorized contaminants.

The method of any preceding clause, wherein the list of water contaminants is provided with a CAS (Chemical Abstracts Service) registration number of each chemical within the list of water contaminants.

The method of any preceding clause, wherein the scoring of the toxicity of the normalized water contaminants comprises executing, via the at least one processor, a machine learning algorithm.

The method of any preceding clause, wherein the machine learning algorithm comprises a neural network.

The method of any preceding clause, the water contaminant data comprising both regulated and unregulated contaminants.

The method of any preceding clause, further comprising: transmitting, from the computer system to a terminal computer in response to a request from the terminal computer, the water toxicity score.

A system comprising: at least one processor; and a non-transitory computer-readable storage medium having instructions stored which, when executed by the at least one processor, cause the processor to perform operations comprising: receiving, from a plurality of sensors within a predefined geographic area, water contaminant data; normalizing, the water contaminant data, resulting in normalized water contaminants; receiving, from a database, a list of categorized contaminants; and scoring, using the list of categorized contaminants, a toxicity of the normalized water contaminants, resulting in a water toxicity score for the predefined geographic area.

The system of any preceding clause, wherein the list of categorized contaminants is generated by: receiving, via web scraping, a list of water contaminants; stratifying the list of water contaminants into categories based on commonalities, resulting in categories of contaminants; and classifying the list of water contaminants into the categories of contaminants, resulting in the list of categorized contaminants.

The system of any preceding clause, wherein the list of water contaminants is provided with a CAS (Chemical Abstracts Service) registration number of each chemical within the list of water contaminants.

The system of any preceding clause, wherein the scoring of the toxicity of the normalized water contaminants comprises executing a machine learning algorithm.

The system of any preceding clause, wherein the machine learning algorithm comprises a neural network.

The system of any preceding clause, the water contaminant data comprising both regulated and unregulated contaminants.

The system of any preceding clause, the non-transitory computer-readable storage medium having additional instructions stored which, when executed by the at least one processor, cause the at least one processor to perform operations comprising: transmitting, to a terminal computer in response to a request from the terminal computer, the water toxicity score.

A non-transitory computer-readable storage medium having instructions stored which, when executed by at least one processor, cause the processor to perform operations comprising: receiving, from a plurality of sensors within a predefined geographic area, water contaminant data; normalizing, the water contaminant data, resulting in normalized water contaminants; receiving, from a database, a list of categorized contaminants; and scoring, using the list of categorized contaminants, a toxicity of the normalized water contaminants, resulting in a water toxicity score for the predefined geographic area.

The non-transitory computer-readable storage medium of any preceding clause, wherein the list of categorized contaminants is generated by: receiving, via web scraping, a list of water contaminants; stratifying the list of water contaminants into categories based on commonalities, resulting in categories of contaminants; and classifying the list of water contaminants into the categories of contaminants, resulting in the list of categorized contaminants.

The non-transitory computer-readable storage medium of any preceding clause, wherein the list of water contaminants is provided with a CAS (Chemical Abstracts Service) registration number of each chemical within the list of water contaminants.

The non-transitory computer-readable storage medium of any preceding clause, wherein the scoring of the toxicity of the normalized water contaminants comprises executing a machine learning algorithm.

The non-transitory computer-readable storage medium of any preceding clause, wherein the machine learning algorithm comprises a neural network.

The non-transitory computer-readable storage medium of any preceding clause, the water contaminant data comprising both regulated and unregulated contaminants.

We claim:

1. A method comprising:

receiving, at a computer system from a plurality of sensors within a predefined geographic area, water contaminant data;

normalizing, via at least one processor of the computer system the water contaminant data, resulting in normalized water contaminants;

receiving, at the computer system from a database, a list of categorized contaminants, wherein the list of categorized contaminants is generated by:

web scraping a list of water contaminants;

stratifying, via the at least one processor executing a neural network, the list of water contaminants into categories based on commonalities, resulting in categories of contaminants, wherein the neural network is trained to identify combinations of toxins formed from individual contaminants; and classifying, via the at least one processor, the list of water contaminants into the categories of contaminants, resulting in the list of categorized contaminants; and scoring, via the at least one processor using the list of categorized contaminants, a toxicity of the normalized water contaminants, resulting in a water toxicity score for the predefined geographic area.

2. The method of claim 1, wherein the list of water contaminants is provided with a CAS (Chemical Abstracts Service) registration number of each chemical within the list of water contaminants.

3. The method of claim 1, wherein the scoring of the toxicity of the normalized water contaminants comprises executing, via the at least one processor, a machine learning algorithm.

4. The method of claim 3, wherein the machine learning algorithm comprises a neural network.

5. The method of claim 1, the water contaminant data comprising both regulated and unregulated contaminants.

6. The method of claim 1, further comprising:

transmitting, from the computer system to a terminal computer in response to a request from the terminal computer, the water toxicity score.

7. A system comprising:

at least one processor; and a non-transitory computer-readable storage medium having instructions stored which, when executed by the at least one processor, cause the processor to perform operations comprising:

receiving, from a plurality of sensors within a predefined geographic area, water contaminant data;

normalizing, the water contaminant data, resulting in normalized water contaminants;

receiving, from a database, a list of categorized contaminants, wherein the list of categorized contaminants is generated by:

web scraping a list of water contaminants;

stratifying, via the at least one processor executing a neural network, the list of water contaminants into categories based on commonalities, resulting in categories of contaminants, wherein the neural network is trained to identify combinations of toxins formed from individual contaminants; and classifying, via the at least one processor, the list of water contaminants into the categories of contaminants, resulting in the list of categorized contaminants; and scoring, using the list of categorized contaminants, a toxicity of the normalized water contaminants, resulting in a water toxicity score for the predefined geographic area.

8. The system of claim 7, wherein the list of water contaminants is provided with a CAS (Chemical Abstracts Service) registration number of each chemical within the list of water contaminants.

9. The system of claim 7, wherein the scoring of the toxicity of the normalized water contaminants comprises executing a machine learning algorithm.

10. The system of claim 9, wherein the machine learning algorithm comprises a neural network.

11. The system of claim 7, the water contaminant data comprising both regulated and unregulated contaminants.

12. The system of claim 7, the non-transitory computer-readable storage medium having additional instructions stored which, when executed by the at least one processor, cause the at least one processor to perform operations comprising:

transmitting, to a terminal computer in response to a request from the terminal computer, the water toxicity score.

13. A non-transitory computer-readable storage medium having instructions stored which, when executed by at least one processor, cause the processor to perform operations comprising:

receiving, from a plurality of sensors within a predefined geographic area, water contaminant data;

normalizing, the water contaminant data, resulting in normalized water contaminants;

receiving, from a database, a list of categorized contaminants, wherein the list of categorized contaminants is generated by:

web scraping a list of water contaminants;

stratifying, via the at least one processor executing a neural network, the list of water contaminants into categories based on commonalities, resulting in categories of contaminants, wherein the neural network is trained to identify combinations of toxins formed from individual contaminants; and classifying, via the at least one processor, the list of water contaminants into the categories of contaminants, resulting in the list of categorized contaminants; and scoring, using the list of categorized contaminants, a toxicity of the normalized water contaminants, resulting in a water toxicity score for the predefined geographic area.

14. The non-transitory computer-readable storage medium of claim 13, wherein the list of water contaminants is provided with a CAS (Chemical Abstracts Service) registration number of each chemical within the list of water contaminants.

15. The non-transitory computer-readable storage medium of claim 14, wherein the scoring of the toxicity of the normalized water contaminants comprises executing a machine learning algorithm.

16. The non-transitory computer-readable storage medium of claim 15, wherein the machine learning algorithm comprises a neural network.

17. The non-transitory computer-readable storage medium of claim 16, the water contaminant data comprising both regulated and unregulated contaminants.

* * * * *